United States Patent [19]
Hardin et al.

[11] Patent Number: 6,017,709
[45] Date of Patent: Jan. 25, 2000

[54] DNA REPLICATION TEMPLATES STABILIZED BY GUANINE QUARTETS

[75] Inventors: Susan Houck Hardin, Bellaire; Jun Ying; Leslie Burgan Jones, both of Houston, all of Tex.

[73] Assignee: University of Houston, Houston, Tex.

[21] Appl. No.: 09/069,434

[22] Filed: Apr. 29, 1998

[51] Int. Cl.$^7$ .............................. C12Q 1/68; C07H 21/02; C07H 21/04; C15N 15/00
[52] U.S. Cl. .......................... 435/6; 536/23.1; 536/24.3; 935/76; 935/77; 935/78
[58] Field of Search ................................ 435/6; 536/23.1, 536/24.3; 935/76, 77, 78

[56] References Cited

U.S. PATENT DOCUMENTS

| | | | |
|---|---|---|---|
| 5,629,154 | 5/1997 | Kim et al. ..................................... | 435/6 |
| 5,643,890 | 7/1997 | Iversen et al. ............................. | 514/44 |
| 5,686,245 | 11/1997 | West et al. ................................... | 435/6 |
| 5,734,040 | 3/1998 | Weeks et al. ........................... | 536/24.5 |

OTHER PUBLICATIONS

Guo et al., Effect of Thymine Tract Length on the Structure and Stability of Model Telomeric Sequences. Biochemistry 32 : 3596–3603 (1993).

Kang et al., Crystal structure of four–stranded Oxytricha telomeric DNA. Nature 356 : 126–131 (1992).

Marsh et al., G–wires : Self–Assembly of Telomeric Oligonucleotide, d(GGGGTTGGGG), into Large Superstructures. Biochemistry 33: 10718–10724 (1994).

Marsh et al., A New DNA Nanostructure, the G–wire, imaged by Scanning Probe Miroscopy. Nucleic Acids Research 23 (4) : 696–700 (1995).

Sen et al., Novel DNA Superstructures formed by Telomere–like Oligomers. Biochemistry 31 : 65–70 (1992).

Smith et al., Quadruplex Structure of Oxytricha Telomeric DNA Oligonucleotides. Nature 356 : 164–168 (1992).

Williamson et al., Monovalent Cation—Induced Structure of Telomeric DNA :The G–Quartet Model. Cell 58 :871–880 (1989).

*Primary Examiner*—Ardin H. Marschel
*Assistant Examiner*—Ethan Whisenant
*Attorney, Agent, or Firm*—Fulbright & Jaworski, L.L.P.

[57] ABSTRACT

Guanine-rich oligonucleotide primers and short telomeric DNA oligonucleotides that serve as non-conventional templates for the synthesis of long, nascent DNA strands are used to screen for pharmaceutical agents. Using the methods of the invention, agents exhibiting antagonistic or agonistic effects on guanine quartet formation can be selected for further study. The invention also provides a predictive assay for cancer in which the level of DNA polymerase activity at a quartet stabilized template is measured. The invention also contributes a method for screening pharmaceutical agents that reduce or inhibit DNA polymerase activity at guanine quartet stabilized templates. The invention provides a method of creating extended DNA molecules from oligonucleotide templates. The invention also provides a method of inhibiting the ageing process in which an oligonucleotide capable of forming non-Watson-Crick structures is used to promote the elongation of telomeres by DNA polymerase.

20 Claims, 5 Drawing Sheets

A
Primer: Yeast  Oxy1.5  Tet1.5  Human
Temp(°C): 20 40 60  20 40 60  20 40 60  20 40 60

B
Primer:      Tet1.5         TetZ7          TetP7         TetZ2479      TetP2479
Temp(°C) c 40 45 50 55 60 c 40 45 50 55 60 c 40 45 50 55 60 c 40 45 50 55 60 c 40 45 50 55 60

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
          (A) LENGTH: 8 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide"

-continued (iii) HYPOTHETICAL: NO (iv) ANTI-SENSE: NO (xi) SEQUENCE DESCRIPTION: SEQ ID NO:1:

GGGATGGG                                                                            8

(2) INFORMATION FOR SEQ ID NO:2:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (xi) SEQUENCE DESCRIPTION: SEQ ID NO:2:

GGAGTGGG                                                                            8

(2) INFORMATION FOR SEQ ID NO:3:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (xi) SEQUENCE DESCRIPTION: SEQ ID NO:3:

GAGGGGCT                                                                            8

(2) INFORMATION FOR SEQ ID NO:4:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (ix) FEATURE:
            (D) OTHER INFORMATION:    N = 7-deaza-deoxyguanine (xi) SEQUENCE DESCRIPTION: SEQ ID NO:4:

GGAGNGAG                                                                            8

(2) INFORMATION FOR SEQ ID NO:5:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (ix) FEATURE:
            (D) OTHER INFORMATION:   N = 2-aminopurine (xi) SEQUENCE DESCRIPTION: SEQ ID NO:5:

GGAGNGAG                                                                    8

(2) INFORMATION FOR SEQ ID NO:6:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (xi) SEQUENCE DESCRIPTION: SEQ ID NO:6:

GGAGGGAG                                                                    8

(2) INFORMATION FOR SEQ ID NO:7:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (xi) SEQUENCE DESCRIPTION: SEQ ID NO:7:

GGAGAGAG                                                                    8

(2) INFORMATION FOR SEQ ID NO:8:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (xi) SEQUENCE DESCRIPTION: SEQ ID NO:8:

GGAGGGTG                                                                    8

(2) INFORMATION FOR SEQ ID NO:9:

(i) SEQUENCE CHARACTERISTICS:
            (A) LENGTH: 8 base pairs

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (iv) ANTI-SENSE: NO (xi) SEQUENCE DESCRIPTION: SEQ ID NO:9:

GGTGGGAG                                                              8

(2) INFORMATION FOR SEQ ID NO:10:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (iv) ANTI-SENSE: NO (xi) SEQUENCE DESCRIPTION: SEQ ID NO:10:

GGTGGGTG                                                              8

(2) INFORMATION FOR SEQ ID NO:11:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (iv) ANTI-SENSE: NO (xi) SEQUENCE DESCRIPTION: SEQ ID NO:11:

GAGGGAGG                                                              8

(2) INFORMATION FOR SEQ ID NO:12:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (iv) ANTI-SENSE: NO (xi) SEQUENCE DESCRIPTION: SEQ ID NO:12:

AGGGAGGG                                                              8

(2) INFORMATION FOR SEQ ID NO:13:

(i) SEQUENCE CHARACTERISTICS:
        (A) LENGTH: 8 base pairs
```

(B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (xi) SEQUENCE DESCRIPTION: SEQ ID NO:13:

GGGAGGGA                                                                                8

(2) INFORMATION FOR SEQ ID NO:14:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (xi) SEQUENCE DESCRIPTION: SEQ ID NO:14:

GGGTTAGGG                                                                               9

(2) INFORMATION FOR SEQ ID NO:15:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (xi) SEQUENCE DESCRIPTION: SEQ ID NO:15:

GGTGTGTGGG TGT                                                                         13

(2) INFORMATION FOR SEQ ID NO:16:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (xi) SEQUENCE DESCRIPTION: SEQ ID NO:16:

GGGGTTGGGG                                                                             10

(2) INFORMATION FOR SEQ ID NO:17:

(i) SEQUENCE CHARACTERISTICS:
            (A) LENGTH: 12 base pairs

```
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (xi) SEQUENCE DESCRIPTION: SEQ ID NO:17:

GGGGTTTTGG GG                                                              12

(2) INFORMATION FOR SEQ ID NO:18:

(i) SEQUENCE CHARACTERISTICS:
            (A) LENGTH:    10 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (ix) FEATURE:
            (D) OTHER INFORMATION:   N = 7-deaza-deoxyguanine (xi) SEQUENCE DESCRIPTION: SEQ ID NO:18:

NNNNTTNNNG                                                                 10

(2) INFORMATION FOR SEQ ID NO:19:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (ix) FEATURE:
            (D) OTHER INFORMATION:   N = 7-deaza-deoxyguanine (xi) SEQUENCE DESCRIPTION: SEQ ID NO:19:

GNGNTTNGNG                                                                 10

(2) INFORMATION FOR SEQ ID NO:20:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (ix) FEATURE:
            (D) OTHER INFORMATION:   N = 2-aminopurine
```

(xi) SEQUENCE DESCRIPTION: SEQ ID NO:20:

NNNNTTNNNG                                                                      10

(2) INFORMATION FOR SEQ ID NO:21:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide"

(iii) HYPOTHETICAL: NO (iv) ANTI-SENSE: NO (ix) FEATURE:
          (D) OTHER INFORMATION:   N = 2-aminopurine (xi) SEQUENCE DESCRIPTION: SEQ ID NO:21:

GNGNTTNGNG                                                                      10

(2) INFORMATION FOR SEQ ID NO:22:

(i) SEQUENCE CHARACTERISTICS:
          (A) LENGTH: 9 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide"

(iii) HYPOTHETICAL: NO (iv) ANTI-SENSE: NO (xi) SEQUENCE DESCRIPTION: SEQ ID NO:22:

CGGCGGCGG                                                                        9

(2) INFORMATION FOR SEQ ID NO:23:

(i) SEQUENCE CHARACTERISTICS:
          (A) LENGTH: 505 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide"

(iii) HYPOTHETICAL: NO (iv) ANTI-SENSE: NO (xi) SEQUENCE DESCRIPTION: SEQ ID NO:23:

GGAGGGAGCC  GACAGATCGT  TGGCGTTGTA  GGAAGGATGC  ACACCCTTGA  GAGCATCCAC    60

GATCTCTTCC  TTGGTAGAAG  AGGGATGCTT  GGCCAGCCAG  GTAGTCACCA  GGCCGATGCG   120

CTGCTTGACT  CCTTTCTCCT  TGGCCACGAA  CGCATACCGA  CCATCGGTGG  TCTTGGTATA   180

GGTCCAGTCG  TTGCTGTTGC  GGGAATGCGA  ACCTTGGAAC  TTGACTTTCT  GGCCCATGTA   240

CATTCATCCT  TCCGACCCGT  TATTCGATGG  GTCAATCGTG  CTTGAGAGAC  TGGTTGAAGT   300

CAGGGTCCGA  CCAGCAAGGA  TCGGACCAAA  ACTCTTCGTA  CTCTTTGCGC  TTGCGGTATT   360

CCGCAAGGTC  GATGACAGGG  GCAGGCATGT  CCTCGTCATC  CAGTTCTTCG  ATGGGAGTCA   420

```
TCGGGTGTAA TCCCGAATCT CATCCTGCCA GTCACGGTCA GACTTGCCGC GCTTCTCGCG    480

CTTGTCCTTG TGCGGTCCTC CCTCC                                          505
```

DNA REPLICATION TEMPLATES STABILIZED BY GUANINE QUARTETS

The work herein was supported, in part, by grants from the United States Government. The United States Government may have certain rights in the invention.

BACKGROUND OF THE INVENTION

Guanine-rich oligonucleotides can spontaneously self-assemble into four-stranded helices in vitro (Sen, D. & Gilbert, W., *Nature* 334:364–366 (1988); Kang, C. et al., *Nature* 356:126–131 (1992)). These four-stranded complexes can further associate into superstructures composed of 8, 12, or 16 oligomers (Sen, D. & Gilbert, W., *Biochemistry* 31:65–70 (1992)). In addition, some guanine-rich oligonucleotides can also assemble in an offset, parallel alignment, forming long "G-wires" (Marsh, T. C. & Henderson, E., *Biochemistry* 33:10718–10724 (1994); Marsh, T. C. et al., *Nucleic Acids Research* 23:696–700 (1995)). These higher order structures are stabilized by G-quartets that consist of four guanosine residues arranged in a plane and held together through Hoogsteen base pairings (FIG. 1A–2). At least three contiguous guanines within the oligomer are critical for the formation of these higher order structures (Sen, D. & Gilbert, W., *Biochemistry* 31:65–70 (1992)). Such guanine-rich sequences exist in HIV-1 RNA sequences (Awang, G. & Sen, D., *Biochemistry* 32:11453–11457 (1993)), immunoglobulin switch regions, and eukaryotic telomeres (Sen, D. & Gilbert, W., *Nature* 334:364–366 (1988)). It has been suggested that four-stranded DNAs have a variety of biological roles, such as inhibition of HIV-1 integrase (Mazumder, A. et al., *Biochemistry* 35:13762–13771 (1996)), formation of synapsis during meiosis (Sen, D. & Gilbert, W., *Nature* 334:364–366 (1988)), and telomere maintenance (Williamson, J. R. et al., *Cell* 59:871–880 (1989); Baran, N. et al., *Nucleic Acids Research* 25:297–303 (1997)).

Telomeres are implicated in pairing sister chromatids (Kolberg, R., J. *NIH Research* 9:24–26 (1997)), chromosome segregation in mitosis (Kirk, K. E. et al., *Science* 275:1478–1481 (1997)), formation of synapsis in meiosis, cell aging (Lundblad, V. & Szostak, J. W., *Cell* 57:633–643 (1989)), and tumorigenesis (Murnane, J. P. et al., *EMBO J.* 13:4953–4962 (1994)). Telomerase is thought to be essential for the maintenance of chromosome ends and, in particular, for the synthesis of telomeric DNA. However, certain telomerase knockout yeast strains can survive and generate a TG1-3 tail in a cell cycle-regulated manner (Lundblad, V. & Blackburn, E. H., *Cell* 73:347–360 (1993); Wellinger, R. J. et al., *Cell* 85:423–433 (1996)). Additionally, some human tumor cell lines without detectable telomerase activity maintain telomeric DNA (Bryan, T. M. et al., *EMBO J.* 14:4240–4248 (1995)). Studies of telomerase RNA knockout mice demonstrate that oncogenically transformed telomerase null mouse cells containing detectably shortened telomeres form tumors in nude mice (Blasco, M. A. et al., *Cell* 91:25–34 (1997)). All of the above indicate that additional mechanisms exist to maintain chromosome ends in vivo.

This invention is based on data that indicates that DNA polymerases appear to be able to recognize and template DNA synthesis from the non-Watson-Crick DNA structures that are proposed to exist at the telomere. This activity explains how immortalized cell lines lacking detectable telomerase activity and telomerase knockout organisms survive and maintain telomere length. DNA synthesis primed from the alternative DNA structures at the telomere provides an additional mechanism for maintaining the integrity of chromosome ends in vivo. It must be noted that short oligonucleotide primers were rapidly extended by the polymerase into several hundred base molecules. This mechanism probably involves alternative DNA base pairings to stabilize replication templates active in promoting expansion of a genome comprised of linear chromosomes and it may have provided a mechanistic scaffold for primitive genome expansion. This mechanism may also influence expansions and contractions occurring during replication of guanine-rich repeats (including triplets) within the genome.

BRIEF SUMMARY OF THE INVENTION

An object of the invention is to provide a method of screening potential therapeutic agents for further investigation by determining the antagonistic activity of the agent for the formation of guanine quartets comprising the steps of priming a sequencing reaction, in the presence of a test agent, with an oligonucleotide capable of forming a non-Watson-Crick structures where the oligonucleotide produces high intensity data (HID) and measuring the amount of HID production. Further objects of the invention utilizing this method provide an oligonucleotide containing at least three contiguous guanine residues. An additional object of the invention utilizing this method provide an oligonucleotide that is an octamer oligonucleotide; an oligonucleotide containing at least five guanine residues, or an oligonucleotide with one of the following sequences: SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

Another object of the invention is to provide a method of screening for potential therapeutic agents by determining the agonistic activity of said agent for the formation of guanine quartets comprising the steps of priming a sequencing reaction, in the presence of a test agent, with an oligonucleotide capable of forming non-Watson-Crick structures in which the oligonucleotide produces high intensity data (HID); and measuring the amount of HID production. Various further objects of the invention provide this method utilizing an oligonucleotide containing at least three contiguous guanine residues; an oligonucleotide which is an octamer oligonucleotide; an oligonucleotide containing at least five guanine residues; or an oligonucleotide with one of the following sequences: SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

Yet another object of the invention is to provide a method of screening for susceptibility to cancer comprising assaying a biopsy extract for increased DNA polymerase activity at a quartet stabilized template wherein the template comprises an oligonucleotide capable of forming non-Watson-Crick structures in which the oligonucleotide produces high intensity data (HID). Various further objects of the invention provide this method utilizing an oligonucleotide containing at least three contiguous guanine residues; an oligonucleotide which is an octamer oligonucleotide; an oligonucleotide containing at least five guanine residues; or an oligonucleotide with one of the following sequences: SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

Another object of the invention provides a method of screening for therapeutic agents that reduce or inhibit DNA polymerase activity templated from guanine quartet stabilized replication templates comprising priming a sequencing reaction, in the presence of a test agent, with an oligonucleotide capable of forming non-Watson-Crick structures in which the oligonucleotide produces high intensity data (HID) in the presence of DNA polymerase and detecting the amount of DNA polymerization. Various further objects of the invention provide this method utilizing an oligonucleotide containing at least three contiguous guanine residues; an oligonucleotide which is an octamer oligonucleotide; an oligonucleotide containing at least five guanine residues; or an oligonucleotide with one of the following sequences: SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

Still another object of the invention provides a method of creating extended DNA molecules templated from an oligonucleotide capable of forming a non-Watson-Crick structure wherein the oligonucleotide produces high intensity data (HID). Various further objects of the invention provide this method utilizing an oligonucleotide containing at least three contiguous guanine residues; an oligonucleotide which is an octamer oligonucleotide; an oligonucleotide containing at least five guanine residues; or an oligonucleotide with one of the following sequences: SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

Another object of the invention is to provide a method of inhibiting the ageing process in which an oligonucleotide capable of forming a non-Watson-Crick structure and producing high intensity data (HID) is used to promote the elongation of telomeres by the action of DNA polymerase. Various further objects of the invention provide this method utilizing an oligonucleotide containing at least three contiguous guanine residues; an oligonucleotide which is an octamer oligonucleotide; an oligonucleotide containing at least five guanine residues; or an oligonucleotide with one of the following sequences: SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

BRIEF DESCRIPTION OF THE DRAWINGS

FIG. 1A-1 shows the chemical structure of a Watson-Crick G-C base pair. FIG. 1A-2 shows the structure of a G-quartet formed through Hoogsteen base pairings. FIG. 1A-3 shows the structures of guanine and its analogs, 7-deaza-dG (Z) and 2-aminopurine (P).

FIG. 2A shows high intensity data (HID) produced by Asub primer in sequencing reactions in the presence or absence of a conventional replication template. Lane 1 shows HID at the beginning of the sequencing data when a conventional template is included in the octamer primed sequencing reaction. Lane 2 shows the result of a sequencing reaction with the pGEM plasmid template and the 18 base, −21 M13 primer. Template-dependent sequence information, but no HID was produced. Lane 3 shows a representative sequencing reaction primed by a non-HID producing octamer. Lane 4 shows HID produced by the Asub primer without a conventional sequencing template.

FIG. 2B shows exonuclease 1 (Exo 1) treatment of reaction components. Octamer primed sequencing reactions were performed after the single-strand nuclease treatments. Lane 1 shows the result of a control sequencing reaction of Asub primer with 10 units of heat inactivated Exo 1. Lane 2 shows the results obtained when heat denatured sequencing reaction premix was quick cooled on ice, 10 units of Exo 1 were added, and the reaction was incubated at 37° C. for 15 minutes. Subsequently, Exo 1 was heat inactivated (15 minutes at 85° C.) and Asub primer was added. Lane 3 shows the results obtained when sequencing reaction premix containing Asub primer was heat denatured and quick cooled on ice, 10 units of Exo 1 were added, the reaction was incubated at 37° C. for 15 minutes, and Exo 1 was heat inactivated. Lane 4 shows a control sequencing reaction of Asub with no Exo 1 treatment.

FIG. 2C shows that HID replication templates are less thermostable than conventional templates. Sequencing reactions were performed using the Asub primer and a dsDNA template at the indicated annealing temperatures.

FIG. 2D shows sequencing reactions using individual Asub variants. Lane 1 Asub: 5' GGAGGGAG 3' (SEQ ID NO:6); Lane 2, ATsub: 5' GGAGGGTG 3' (SEQ ID NO:8); Lane 3, TAsub: 5' GGTGGGAG 3' (SEQ ID NO:9); Lane 4, Tsub: 5' GGTGGGTG 3' (SEQ ID NO:10); Lane 5, A3sub: 5' GGAGAGAG 3' (SEQ ID NO:7); Lane 6, P1: 5' GAGGGAGG 3' (SEQ ID NO:11); Lane 7, P2: 5' AGGGAGGG 3' (SEQ ID NO:12); Lane 8, P3: 5' GGGAGGGA 3' (SEQ ID NO:13). Sequencing reactions were assembled without conventional DNA templates and processed using octamer primed sequencing conditions.

FIG. 3 shows that telomeric DNA oligonucleotides template HID. FIG. 3A shows octamer primed sequencing conditions were used in reactions of telomeric sequences from human (5' GGGTTAGGG 3' (SEQ ID NO:14), yeast (5' GGTGTGTGGGTGT 3' (SEQ ID NO:15)), Tetrahymena (Tet1.5, 5' GGGGTTGGGG 3' (SEQ ID NO:16)) and Oxytricha (Oxy1.5, 5' GGGGTTTTGGGG 3' (SEQ ID NO:17)) without dsDNA templates. Reactions were cycled using the indicated annealing temperature.

FIG. 3B shows HID thermostability profiles of Tet1.5, the 7-deaza-dG substitutions, TetZ7 (5' ZZZZTTZZZG 3' (SEQ ID NO:18)) and TetZ2479 (5' GZGZTTZGZG 3' (SEQ ID NO:19)), and the 2-AP substitutions, TetP7 (5' PPPPTTP-PPG 3' (SEQ ID NO:20)) and TetP2479 (5' GPGPTTPGPG 3' (SEQ ID NO:21)). Sequencing reactions were cycled using the indicated annealing temperature. 'C' indicates lanes containing sequencing reactions of pGEM plasmid template and the 18 base, −21 M13 primer.

Figure 1A:
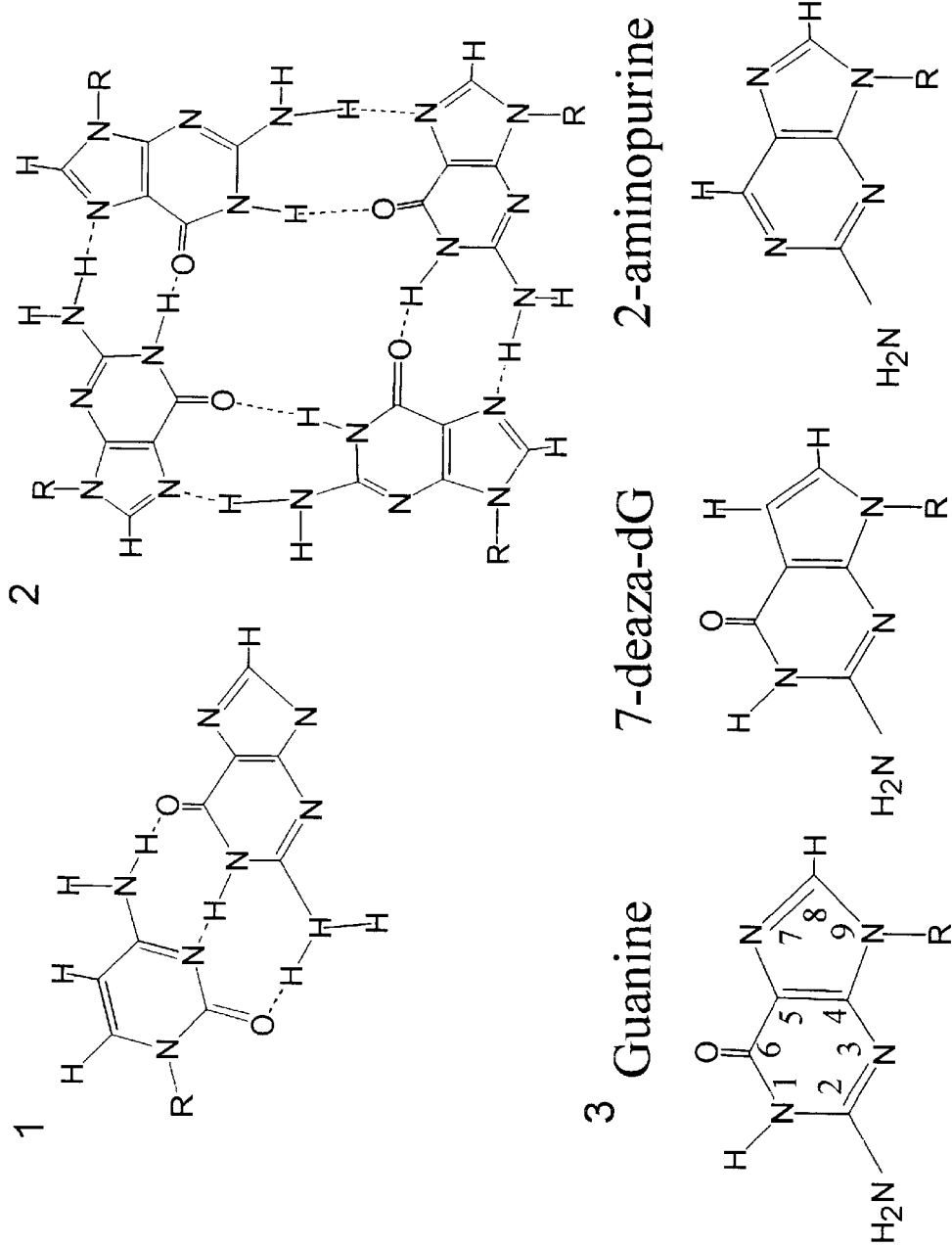
FIG. 1A shows a variety of chemical structures related to Asub octamer.

The drawings are not necessarily to scale. Certain features of the invention may be exaggerated in scale or shown in schematic form in the interest of clarity and conciseness.

DETAILED DESCRIPTION OF THE INVENTION

It will be readily apparent to one skilled in the art that various substitutions and modifications may be made to the invention disclosed herein without departing from the scope and spirit of the invention.

As used herein, an "agonist" is a factor which interacts to promote or stimulate the action or effect of other molecules or factors.

As used herein, an "antagonist" is a factor which neutralizes or impedes the action or effect of other molecules or factors.

As used herein, a "biopsy extract" is a solubilized portion of biological material or tissue removed from a patient.

As used herein, "high intensity data," or HID, is very intense, but unreadable DNA sequence data.

As used herein, a "therapeutic agent" is a molecule or compound which can be used to reverse, inhibit, or slow the progress of a medical condition, or its symptoms. A therapeutic agent need not cure the underlying condition.

One embodiment of the invention provides a method of screening for potential therapeutic agents by determining the antagonistic activity of the agent for the formation of guanine quartets comprising the steps of priming a sequencing reaction, in the presence of a test agent, with an oligonucleotide capable of forming non-Watson-Crick structures where the oligonucleotide produces high intensity data (HID) and measuring the amount of HID production. Other embodiments of the invention utilize an oligonucleotide containing at least three contiguous guanine residues. A further embodiment of the invention utilizes an oligonucleotide that is an octamer oligonucleotide; an oligonucleotide containing at least five guanine residues, or an oligonucleotide with one of the following sequences: SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

Another embodiment of the invention provides a method of screening for therapeutic agents by determining the agonistic activity of said agent for the formation of guanine quartets comprising the steps of priming a sequencing reaction, in the presence of a test agent, with an oligonucleotide capable of forming a non-Watson-Crick structures wherein said oligonucleotide produces high intensity data (HID); and measuring the amount of HID production. Various further objects of the invention provide this method utilizing an oligonucleotide containing at least three contiguous guanine residues; an oligonucleotide which is an octamer oligonucleotide; an oligonucleotide containing at least five guanine residues; or an oligonucleotide with one of the following sequences: SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

The aforementioned embodiments are based on the fact that guanine quartets may have several roles, such as inhibition of HIV-1 integrase, formation of synapsis during meiosis and telomere maintenance. Compounds exhibiting agonistic and antagonistic effects on quartet formation are candidates for further study. These embodiments of the present invention encompass screening assays to select compounds as therapeutic agents.

Yet another embodiment of the invention provides a method of screening for susceptibility to cancer comprising assaying a biopsy extract for increased DNA polymerase activity at a quartet stabilized template wherein the template comprises an oligonucleotide capable of forming a non-Watson-Crick structures in which the oligonucleotide produces high intensity data (HID). Various further embodiments of the invention utilize an oligonucleotide containing at least three contiguous guanine residues; an oligonucleotide which is an octamer oligonucleotide; an oligonucleotide containing at least five guanine residues; or an oligonucleotide with one of the following sequences: SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

Still another embodiment of the invention provides a method of screening for therapeutic agents that reduce or inhibit DNA polymerase activity templated from guanine quartet stabilized replication templates comprising contacting said agents with an oligonucleotide capable of forming a non-Watson-Crick structures wherein said oligonucleotide produces high intensity data (HID) in the presence of DNA polymerase and detecting the amount of DNA polymerization. Various further embodiments along this line utilize an oligonucleotide containing at least three contiguous guanine residues; an oligonucleotide which is an octamer oligonucleotide; an oligonucleotide containing at least five guanine residues; or an oligonucleotide with one of the following sequences: SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

Another embodiment of the invention yields a method of creating extended DNA molecules templated from an oligonucleotide capable of forming a non-Watson-Crick structure wherein said oligonucleotide produces high intensity data (HID). Various further embodiments of this aspect utilize an oligonucleotide containing at least three contiguous guanine residues; an oligonucleotide which is an octamer oligonucleotide; an oligonucleotide containing at least five guanine residues; or an oligonucleotide with one of the following sequences: SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

An additional embodiment of the invention is a method of inhibiting the ageing process wherein an oligonucleotide capable of forming a non-Watson-Crick structure and producing high intensity data (HID) is used to promote the elongation of telomeres by the action of DNA polymerase. Various further embodiments of this mode utilize an oligonucleotide containing at least three contiguous guanine residues; an oligonucleotide which is an octamer oligonucleotide; an oligonucleotide containing at least five guanine residues; or an oligonucleotide with one of the following sequences: SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

As is evidenced by the embodiments of the invention detailed above, several objects of the invention utilize oligonucleotide primers capable of serving as templates for DNA synthesis, or capable of serving as inhibitors of non-Watson Crick template synthesis. Many of these oligonucleotide primers comprise at least three contiguous guanine residues, and these primers are sufficient to serve as templates for DNA synthesis. Furthermore, many of these are octamer oligonucleotide primers contain at least three contiguous guanine residues. The invention also provides longer oligonucleotide primers that are guanine rich, but do not necessarily contain three consecutive guanine residues.

Certain embodiments of the invention utilize oligonucleotide primers analogous to those mentioned above, in which one or more of the guanine residues is substituted by 7-deaza-dG or 2-AP. These primers are capable of interfering with template formation. These primers can be used as negative controls in a screening system.

The various embodiments of the invention, depending on their purpose may utilize one or more of the following oligonucleotide primers: SEQ ID NO:1 (GGGATGGG), SEQ ID NO:2 (GGAGTGGG), SEQ ID NO:3 (GAGGGGCT), SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21.

As is evidenced by the embodiments of the invention detailed above, several embodiments of the invention utilize oligonucleotide primers capable of serving as templates for DNA synthesis, or capable of serving as inhibitors of non-Watson Crick template synthesis. Many of these oligonucleotide primers comprise at least three contiguous guanine residues, and these primers are sufficient to serve as templates for DNA synthesis. The invention also provides longer oligonucleotide primers that are guanine rich, but do not necessarily contain three consecutive guanine residues.

The following examples are offered by way of illustration and are not intended to limit the invention in any manner.

EXAMPLE 1

HID Production

Figure 2:
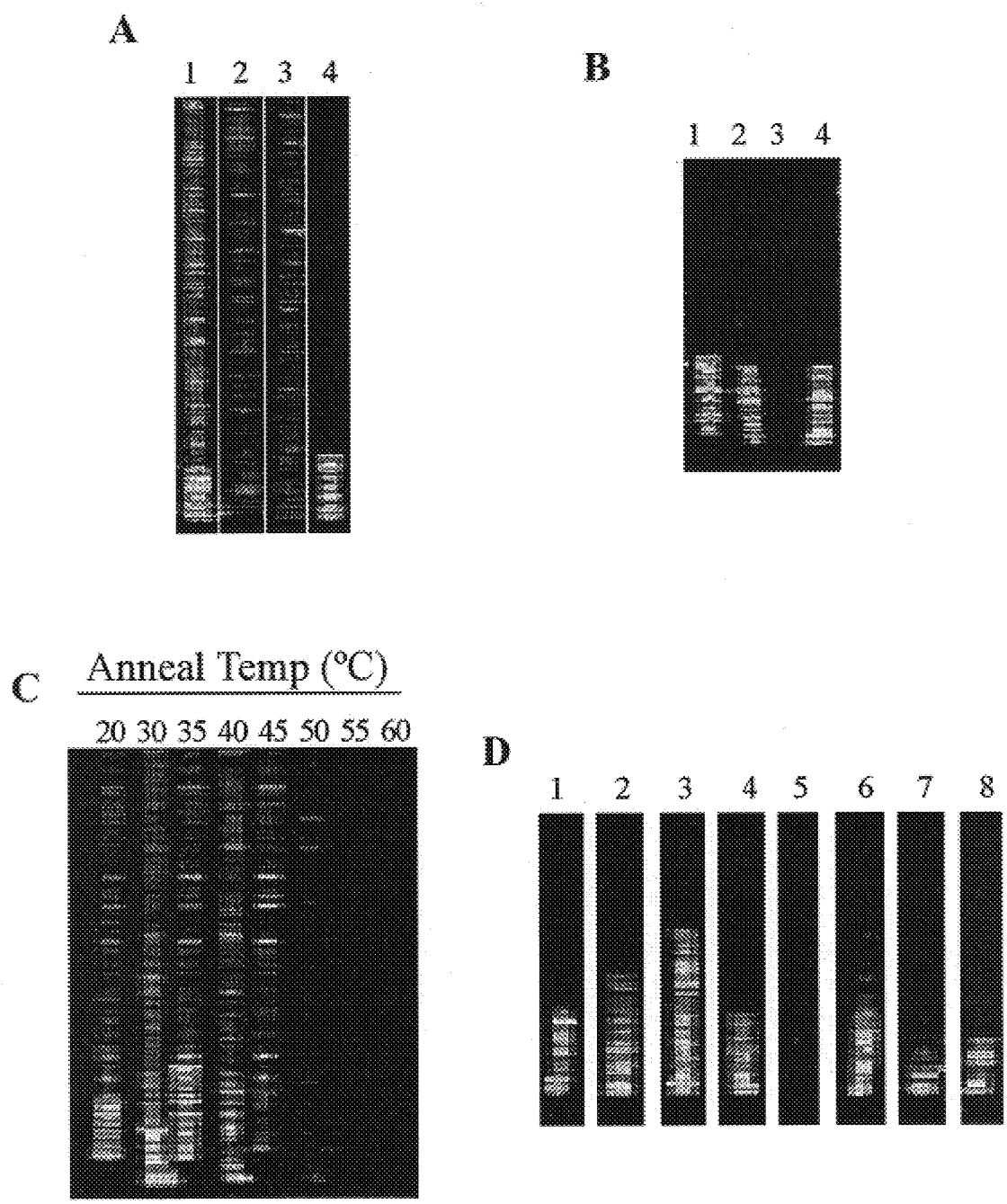

During the development of a DNA sequencing strategy using octamer oligonucleotides as primers for fluorescent dye-terminator, cycle sequencing reactions, several oligonucleotides produced an unusual sequencing profile. Sequencing reactions were cycled on a Perkin Elmer Gene Amp PCR system 9600 using a 40° C. annealing temperature. Data was collected on an ABI377 Automated DNA Sequencer and is presented in compressed gel file format. Intense, but unreadable, sequence data termed high intensity data (HID) appeared at the beginning of the sequence read, after which normal intensity, high quality, sequence information was observed (FIG. 2A, lane 1). Signal intensity profiles for sequencing reactions primed either by other octamers or by a more typical 18 base primer showed relatively uniform signal intensities from the beginning to the end of data collection (FIG. 2A, lanes 2 and 3). The HID observed indicates that an amplification of short DNAs with seemingly random fluorescent-terminating residues occurs during the cycle sequencing reaction.

To gain more insight into HID production, sequencing reactions were performed using HID-producing octamers without the addition of a conventional DNA template (FIG. 2A, lane 4). Each of these octamers was sufficient to produce the high-intensity sequence products. The primers are clearly responsible for the HID, but Watson-Crick DNA base pairing can not occur between individual octamer primers. Therefore, the amplification is likely due to a higher order G-quartet stabilized structure.

EXAMPLE 2

HID is Not Templated by Contaminating DNA

Four lines of evidence show that the HID is not templated by contaminating DNA from any of the reaction components. First, among the 157 octamers that primed sequencing reactions, only 4 produced HID. Second, sequencing reaction premix that was heat denatured, cooled, and treated with exonuclease I prior to the addition of octamer primer still produced HID (FIG. 2B, lane 2). However, if the primer was added prior to exonuclease treatment, production of the HID was eliminated (FIG. 2B, lane 3). Third, the HID producing octamer "Asub" was synthesized by three companies and each produced HID. Finally, if the annealing temperature of the reaction was increased, HID production was eliminated, but conventionally primed sequence data was unaffected (FIG. 2C). The preferential elimination of HID demonstrates that the structure formed by Asub is less thermostable, and therefore different, than that produced from a conventional priming event at a Watson-Crick duplex. Taken together, these results suggest that HID is generated from higher order structures formed by the interactions among primer molecules.

A clue to the mechanism behind HID formation came from the 3' end of the HID sequence read. It was consistently observed that all HID data was accompanied by the Watson-Crick complement of the HID-producing primer in this region. It should also be noted that a HID-producing reaction resembles one in which the primer starts synthesis from two locations at once (a doubly primed reaction). The HID observed was likely produced from a double stranded DNA (dsDNA) template containing the primer sequence at each 5' end (and the Watson-Crick complement at each 3' end) and was the result of a single primer PCR amplification. DNA polymerase is somehow able to recognize structures comprised of these short, G-rich oligonucleotides as appropriate replication templates and to produce the initial, extended DNA strand seemingly without a primer. The extended DNA strands subsequently serve as templates for the PCR.

EXAMPLE 3

Analysis of Asub Variants

Analysis of the HID-producing octamer sequences suggested that both guanine richness and the presence of at least three consecutive guanines are important for HID production. Since Asub has minimal sequence complexity, variants of this primer were assayed to determine whether its sequence per se or the guanines it contains are important for HID production. Independent sequencing reactions were assembled using octamers Asub (GGAGGGAG (SEQ ID NO:6)), ATsub (GGAGGGTG (SEQ ID NO:8)), TAsub (GGTGGGAG (SEQ ID NO:9)), or Tsub (GGTGGGTG (SEQ ID NO:10)), without the addition of a conventional sequencing template (FIG. 2D, lanes 1–4). The reactions were cycled using conditions in which only a perfectly matched octamer would prime a conventional sequencing template, and analyzed for the production of HID. Each of these substituted octamers produced HID, demonstrating that guanines rather than adenines or thymines are required for HID production (FIG. 2D). There is a critical requirement for three consecutive Gs in the octamer, since elimination of the G track from Asub abolishes HID even at reduced annealing temperatures (FIG. 2D, lane 5). However, the position of the triple G track in the Asub sequence is not critical, since each permutation of Asub produces HID (FIG. 2D, lanes 6–8). Thus, HID production is a highly-ordered phenomenon in which guanine triplets are integral in the formation of the DNA structure recognized by the polymerase.

These results indicate that alternative, non-Watson-Crick base paired DNA structures are formed by the octamer primers and that these structures are recognized by DNA polymerase during sequencing reactions. Since the properties of the HID-producing primers (i.e. guanine richness and presence of at least three consecutive guanines) are similar to those of oligomers known to form four-stranded DNAs, it is very likely that similar DNA quadruplexes are formed from the guanine-rich octamers, and that these structures are stabilized by G-quartets.

EXAMPLE 4

Substitution Studies

Figure 1B:
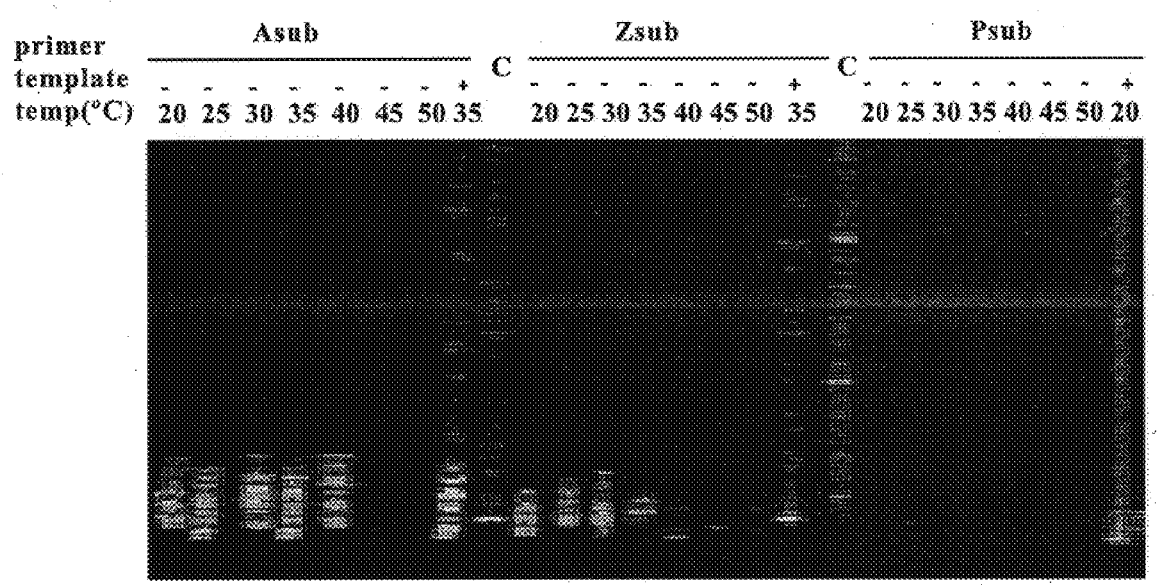
FIG. 1B shows that Guanine N1, O6, and N7 are involved in stabilizing the higher order structures formed by the Asub primer. The fourth guanine in Asub was substituted with either 7-deaza-dG (Zsub, GGAGZGAG (SEQ ID NO:4)) or 2-AP (Psub, GGAGPGAG (SEQ ID NO:5)). Reactions using these oligonucleotides were performed at the indicated annealing temperatures. With a conventional dsDNA template present, both Asub and Zsub oligos primed the reaction from the sequence 5' GGAGGGAG 3' (SEQ ID NO:6), while Psub primed from the sequence 5' GGAGAGAG 3' (SEQ ID NO:7). "C" indicates lanes containing sequencing reactions of pGEM plasmid template and the 18 base, −21 M13 primer.

Atomic mutagenesis was used to identify positions within guanine that stabilize the replication template. In Asub the central base in the guanine triplet is essential for the HID production. Therefore, this position was substituted with either 7-deaza-deoxyguanine (7-deaza-dG) or 2-aminopurine (2-AP). 7-deaza-dG was chosen since guanine N7 is replaced with a carbon atom, changing this position from a hydrogen acceptor to a neutral C-H site (FIG. 1A). Oligonucleotides with 7-deaza-dG are known to prime Watson-Crick templated sequence data (See e.g., Jensen, M. A. et al., DNA Sequence 1:233–239 (1991). The 7-deaza-dG substituted Asub primer, "Zsub," reduced HID thermostability, but maintained the ability to prime conventionally templated extension products (FIG. 1B). Thus, N7 is a position that stabilizes the template responsible for HID production. 2-AP was chosen since it eliminated guanine O6 and H1, positions critical for G—G recognition in Hoogsteen base pairing (FIG. 1A). This modified base eliminated HID production, but not the ability to prime conventionally templated extension products (FIG. 1B). Thus, O6 and H1 are positions essential for stabilization of the replication template. Both 7-deaza-dG and 2-AP substitutions are predicted to decrease the stability of Hoogsteen base pairing by altering one of the two hydrogen bonds comprising a Hoogsteen base pair. Consequently, these data identify Hoogsteen base pairings as stabilizing forces in the structure recognized by the DNA polymerase.

Hoogsteen interactions stabilize parallel-stranded duplexes, triplexes and G-quartets. However, triplex formation requires the presence of an additional pyrimidine-rich third strand which is lacking from the assay. Also, due to both the elevated temperatures at which HID is observed and the length of the resulting products, the structure likely to be stable in these conditions, and, therefore relevant for the polymerase activity detected in these systems is a G-quartet structure. Although no DNA polymerase has been reported to template synthesis from a structure other than a primer-template junction (specifically from an antiparallel DNA duplex), this data is most consistent with polymerase recognition of a structure stabilized by G-quartets.

EXAMPLE 5

Ability of Short Telomeric Sequence Oligonucleotides to Template HID

Figure 3:
Figure 3:
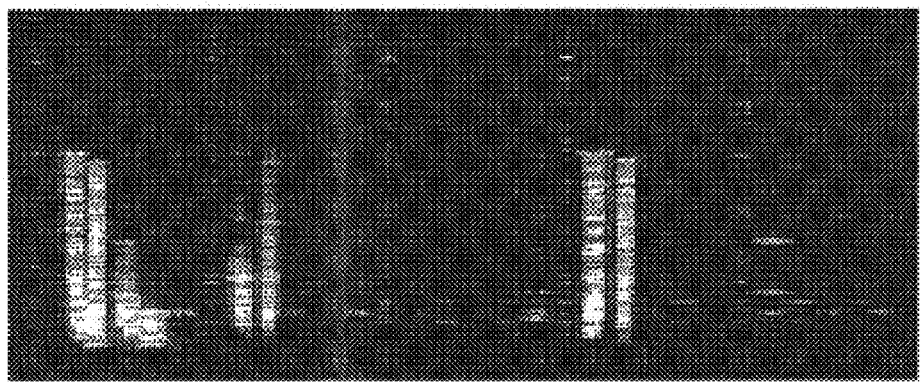

Short telomeric repeats are known to associate into higher order structures stabilized by G-quartets in vitro. (See e.g., Kang, C. et al., Nature 356:126–131 (1992); Marsh, T. C. & Henderson, E., Biochemistry 33:10718–10724 (1994); Marsh, T. C. et al., Nucleic Acids Research 23:696–700 (1995); Williamson, J. R. et al., Cell 59:871–880 (1989); Guo, Q. et al., Biochemistry 32:3596–3603 (1993); Smith, F. W. & Feigon, J., Nature 356:164–167 (1992)). Because the sequences assayed in this detection system are similar to those found at telomeres (in that they are guanine rich in one strand and contain guanine triplets), short telomeric sequence oligonucleotides from yeast (GGTGTGTGGGTGT (SEQ ID NO:15)), Oxytricha (GGGGTTTTGGGG (SEQ ID NO:17)); Tetrahymena (GGGGTTGGGG (SEQ ID NO:16)) and human (GGGTTAGGG (SEQ ID NO:14)) were assayed for their ability to template HID. As evidenced by the production of HID, each of these telomeric sequences formed a structure that is recognized by Taq DNA polymerase (FIG. 3A). Although the length of the HID produced by the same oligonucleotide varied in the different reactions, both the length and thermostability of the HID were dependent on the length of the G-rich oligonucleotide and not on the length of the extended polymer.

EXAMPLE 6

Structure Stabilization

Atomic mutagenesis of Tet1.5 confirms the involvement of guanine H1, O6 and N7 in structure stabilization (FIG. 3B). In one series of oligonucleotides, all except the 3' guanine were substituted with either 7-deaza-dG or 2-AP. In another series of oligonucleotides, guanines at the second, fourth, seventh, and ninth positions in the sequence were substituted with either 7-deaza-dG or 2-AP. Consistent with the data obtained using the mutagenized Asub primers, reduced thermostability is observed when 7-deaza-dG is substituted for guanine, while no HID is observed when 2-AP is similarly substituted (FIG. 3B).

EXAMPLE 7

Scanning Force Microscopy

Figure 4:
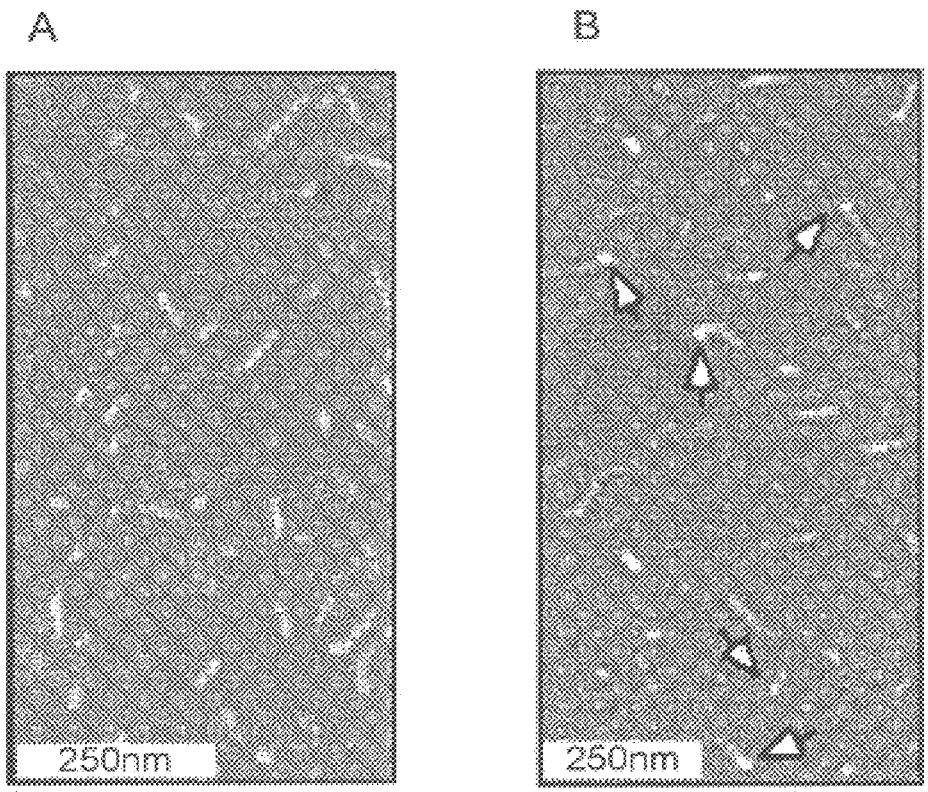
FIG. 4A shows SFM imaging of the G-wires formed from Tet1.5 oligonucleotide (5' GGGGTTGGGG 3' (SEQ ID NO:16)).
FIG. 4B shows the SFM imaging of the binding of AmpliTaq, FS, DNA polymerase to the G-wires. Arrows indicate representative polymerase locations.

Scanning force microscopy (SFM) was used to image directly the DNA structures formed by wild-type Tet1.5 oligonucleotide and to detect interactions between these oligonucleotides and DNA polymerase. Tet1.5 primers were mixed in DNA sequencing reaction buffer at the concentration of 15 pmol/$\mu$l, denatured at 96° C. for 2 minutes, and incubated at 40° C. for 20 hours. Reactions were adsorbed to a freshly cleaved mica surface, washed with ddH$_2$O, dried with nitrogen, and imaged using multi-wall nanotube probe tips in tapping mode on a Digital Instruments Nanoscope III. Higher-order DNA structures, similar to G-wires, are observed in the Tet1.5 oligonucleotide samples (FIG. 4A).

Under these assay conditions, the average height measurement for the Tet1.5 structures was 1.85 nm+/−0.14 nm (number of structures measured, "n," is 86). These measurements are significantly increased over those determined for plasmid DNA under identical conditions (0.55 nm+/−0.12 nm). The lengths of the Tet1.5 G-wires range from 10 nm to 170 nm (30–500 bases, assuming 3.4 angstroms between bases), which is consistent with the HID lengths observed. DNA widths appear larger in SFM that the measured heights, both with traditionally pyramidal tips and with nanotube tips, because the tip dimensions must be convoluted against the sample. A companion SFM sample, into which DNA polymerase was added just prior to adsorbing onto the mica surface, demonstrated that the DNA polymerase interacted with these non-conventional structures (FIG. 4B). DNA polymerase formed complexes at the ends of G-wires more frequently than would be anticipated for random association. Out of 103 G-wire:polymerase complexes sampled, 68 had end-complexes. Making a conservative estimate that the G-wires are 6 times as long as the polymerase, a model in which the polymerase can complex at any of six sites was made and predicted 34.3 end-complexes, half the number observed.

The Tet1.5 oligonucleotide variants containing either 7-deaza-dG or 2-AP substitutions were similarly imaged. The average height of TetZ2479 is 2.35 nm+/−0.40 nm (n=250), and the average height of TetZ7 is 1.12 nm+/−0.62 nm (n=24). However, neither of these oligonucleotides forms long wire structures. This is consistent with the hypothesis that the extended, quartet-stabilized structures are less likely to form or remain stable if guanine N7 is removed. The non-HID producing oligonucleotides containing 2-AP show neither extended structures nor height measurements greater than ~0.7 nm+/−0.40 nm (TetP7, n=248; TetP2479, n=881). Thus, there is a strong correlation between the ability of a oligonucleotide to produce HID and the ability of that oligo to form G-wires.

These results can not be explained by the current model for DNA replication. Therefore, there is a mechanism for DNA replication of templates stabilized through G-quartets. Specifically, since the relevant structures are held together by alternative base pairings, DNA polymerase templates synthesis by binding to and using an oligomer at the 3' end of the polymer as the replication primer, looping back and melting one edge of the quartet structure to access the bases and template the synthesis of a nascent strand. In the assay systems described previously, the G-rich oligonucleotides acted as splints (stabilized through Hoogsteen base pairings) to produce an extended polymer that is recognized as a replication template by the DNA polymerase. The ability to use DNA structures stabilized through guanine quartets as replication templates is biologically relevant, since these types of structures are proposed to exist at the telomere (See e.g., Williamson, J. R. et al., *Cell* 59:871–880 (1989)).

The parallel quartet structure formed by the sequence TGGGGT has been solved to 1.2 angstroms resolution (See e.g., Laughlan, G. et al., *Science* 265:520–524 (1994)), and reveals details of the molecule that may be critical for recognition by the DNA polymerase: Each side of the quartet has dimensions similar to a DNA duplex minor groove. These dimensions may be important for the polymerase activity detected in the assay systems of this invention, since a Taq DNA polymerase:DNA co-crystal was solved (See e.g., Eom, S. H. et al., *Nature* 382:278–281 (1996)) and demonstrates that polymerase binds to the minor groove of a DNA duplex. Thus, although the overall DNA structure is non-conventional, the polymerase recognizes its conventional binding structure for templating DNA synthesis.

EXAMPLE 8

Automated Octamer DNA Sequencing Procedure

Standard sequencing reactions were performed in 10 µl reaction mix containing 25 pmol octamer primer, 200 ng plasmid template and 4 µl Perkin Elmer Dye Terminator Cycle Sequencing premix. Assembled reactions were cycled on a Perkin Elmer GeneAmp PCR System 9600 for 99 cycles at 96° C. for 10 sec, 40° C. for 1 min and 60° C. for 4 min. The sequencing products were stored at −20° C. for no more than two weeks before sodium acetate/ethanol precipitation. The DNA pellets were resuspended in 3.0 µl of loading buffer, 1.5 µl was loaded onto a sequencing gel, and the data was collected by an ABI PRISM 377 DNA Sequencer.

EXAMPLE 9

Different Base Incorporation for Guanine Quartet Stabilized Structures

A 505 bp Asub product from two independent PCRs was cloned and sequenced (SEQ ID NO:23). The sequences of these clones contain the Asub primer at the 5' ends of the inserts. However, the intervening sequence is not obviously related to Asub primer, is unmatched with any sequence in GenBank, but is shared between these clones. These Asub insert sequences were used to design two 17 base primers to probe the PCR for any contaminating DNA. The 17 base primers amplify the expected 492 bp product when the cloned plasmid DNA is added to the PCR but, importantly, they fail to amplify this product if the plasmid DNA is not added. PCRs—performed at either low or high stringency—have failed to provide evidence of contaminating DNA.

This data demonstrates that DNA polymerase templates synthesis from alternatively structured DNA. The data indicates that the polymerase incorporates in a very specific, yet unexpected, manner, since the products cloned from two independent PCRs are essentially identical. The polymerase probably does not read the template bases properly (ie. in a Watson-Crick fashion). Specifically, since N7 is critical for high intensity data production, Hoogsteen base pairings are implicated in structure stabilization. If hydrogen bonding patterns are used by the polymerase to identify and incorporate the complementary base and if a portion of the base that defines these patterns (the Watson-Crick face of the base) is involved in the alternative base pairings that stabilize overall DNA structure, "standard" hydrogen bonding patterns would not be available to the polymerase without destabilizing or, potentially, dissociating the structured polymer. Additionally, the bases may be positioned differently in this alternative polymer. The may be in either anti or syn position (or both), and they may be tilted due to distortions in glycosidic angles. The production of high intensity data is an in vitro selection for a structure comprised of short oligonucleotides that remains associated stably enough to template the initial, continuous DNA polymer. This selective pressure and the proposed differences in DNA base positioning may result in alternate rules for base incorporation.

Additionally, a nonamer oligonucleotide was synthesized with the human triplet repeat sequence (5' CGG CGG CGG 3' (SEQ ID NO:22)) and was assayed for its ability to template HID. This primer was of particular interest because if Watson-Crick base pairing rules are followed for the replication of templates stabilized by guanine-quartets, it would template only incorporation of C and G. It was also of interest because related sequences were previously characterized and shown to form four-stranded DNAs (Fry, M. and Loeb, L. A., *Proc. Natl. Acad. Sci. USA* 91:4950–4954 (1994). When used in the sequencing assay the data was characteristic of HID (in that it was a doubly primed reaction with the complement of the primer present at the 3' end of the sequence). Importantly, the presence of all four colors in the HID indicates that all four bases were incorporated, demonstrating that alternative rules for base incorporation exist for guanine-quartet stabilized replication templates.

EXAMPLE 10

Screening Assay

A sequencing reaction is performed in the presence of varying concentrations of a test substance. The DNA sequencing reaction may be any of those known in the art, including commercially available sequencing kits and methods, as long as the method incorporates a step in which DNA is synthesized. The sequencing primer is an oligonucleotide primer, which can be of varying length, but the primer must be of a type capable of forming guanine quartets.

The sequencing reaction with the guanine quartet capable primer is performed according to the known procedure, except that varying amounts of test agent are added to the sequencing mixture. The range of concentrations tested, varies according to the known properties of the test substance, including, but not limited to, solubility and toxicity properties. A test agent is considered an agonist if it increases the amount of HID observed after the sequencing step is performed. A test agent is considered an antagonist if the degree or intensity of the HID is reduced, or disappears altogether. Any method known in the art for comparing the intensity of sequencing bands can be used to create a basis for comparison.

EXAMPLE 11

Cancer Screening

Cancer screening is performed by comparing the amount of DNA polymerase activity observed in the presence of a quartet stabilized template. A solubilized biopsy extract, or other biological material is assayed by adding an oligonucleotide capable of forming guanine quartets. The level of DNA polymerase activity in the test sample is compared to levels observed in control samples. An increased level of DNA polymerase activity is indicative of a risk factor for cancer, and can actually indicate the presence of the disease itself.

EXAMPLE 12

Screening Assay for Molecules Affecting DNA Polymerase Activity

A sequencing reaction is performed in the presence of varying concentrations of a test substance. The DNA sequencing reaction may be any of those known in the art, including commercially available sequencing kits and methods, as long as the method incorporates the use of DNA polymerase. The sequencing primer is an oligonucleotide primer which can be of varying length, but the primer must be of a type capable of forming guanine quartets.

The sequencing reaction with the guanine quartet capable primer is performed according to the known procedure, except that varying amounts of test agent are added to the sequencing mixture. The range of concentrations tested varies according to the known properties of the test substance, including, but not limited to, solubility and toxicity properties. A test agent is considered an agonist if increased DNA polymerase activity is noted. A test agent is considered an antagonist if a decreased level of DNA polymerase activity is noted. Any method known in the art for measuring DNA polymerase activity can be used, although the most simple and preferred method is to measure the amount of DNA polymerization.

EXAMPLE 13

Creating Extended DNA Molecules

Extended DNA molecules can be created by using any oligonucleotide capable of forming a non-Watson-Crick structure that leads to the production of HID. This reaction utilizes any known procedure for polymerizing DNA that requires a template molecule. The method is accomplished by substituting the oligonucleotide mentioned above in place of the standard primer.

EXAMPLE 14

Inhibiting the Ageing Process

Administration of a dosage of oligonucleotide to a patient is performed in which the oligonucleotide administered is an oligonucleotide capable of forming a non-Watson-Crick structure that leads to the production of HID. The oligonucleotide is administered in a pharmaceutically suitable vehicle. The dosage of oligonucleotide administered will vary from patient to patient.

---

We claim:

1. A method of screening for potential therapeutic agents by determining the antagonistic activity of said agent for the formation of guanine quartets comprising the steps of:

priming a sequencing reaction, in the presence of a test agent, with an oligonucleotide wherein said oligonucleotide forms a non-Watson-Crick structure and wherein said oligonucleotide produces high intensity data (HID); and measuring the amount of HID production wherein a decrease in or elimination of the HID is indicative of antagonistic activity.

2. The method of claim 1 wherein said oligonucleotide contains at least three contiguous guanine residues.

3. The method of claim 1, wherein said oligonucleotide is an octamer oligonucleotide.

4. The method of claim 1, wherein said oligonucleotide contains at least five guanine residues.

5. The method of claim 1 wherein the sequence of said oligonucleotide is SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

6. A method of screening for potential therapeutic agents by determining the agonistic activity of said agent for the formation of guanine quartets comprising the steps of:

priming a sequencing reaction, in the presence of a test agent, with an oligonucleotide wherein said oligonucleotide forms a non-Watson-Crick structure and wherein said oligonucleotide produces high intensity data (HID); and measuring the amount of HID production wherein an increase in the HID is indicative of agonistic activity.

7. The method of claim 6 wherein said oligonucleotide contains at least three contiguous guanine residues.

8. The method of claim 6, wherein said oligonucleotide is an octamer oligonucleotide.

9. The method of claim 6, wherein said oligonucleotide contains at least five guanine residues.

10. The method of claim 6 wherein the sequence of said oligonucleotide is SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

11. A method of screening for therapeutic agents that reduce or inhibit DNA polymerase activity templated from guanine quartet stabilized replication templates comprising contacting said agents with an oligonucleotide wherein said oligonucleotide forms a non-Watson-Crick structure and wherein said oligonucleotide produces high intensity data (HID) in the presence of DNA polymerase; measuring the amount HID production; and detecting the amount of DNA polymerization.

12. The method of claim 11 wherein said oligonucleotide contains at least three contiguous guanine residues.

13. The method of claim 11, wherein said oligonucleotide is an octamer oligonucleotide.

14. The method of claim 11, wherein said oligonucleotide contains at least five guanine residues.

15. The method of claim 11, wherein the sequence of said oligonucleotide is SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, or SEQ ID NO:23.

16. A method of creating extended DNA molecules from an oligonucleotide wherein said oligonucleotide forms a non-Watson-Crick structure and wherein said oligonucleotide produces high intensity data (HID) comprising the step of extending said oligonucleotide in the presence of DNA polymerase.

17. The method of claim 16 wherein said oligonucleotide contains at least three contiguous guanine residues.

18. The method of claim 16, wherein said oligonucleotide is an octamer oligonucleotide.

19. The method of claim 16, wherein said oligonucleotide contains at least five guanine residues.

20. The method of claim 16, wherein the sequence of said oligonucleotide is SEQ ID NO:1, SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:22, SEQ ID NO:23.

* * * * *